United States Patent [19]

Mueller et al.

[11] Patent Number: 5,321,189
[45] Date of Patent: Jun. 14, 1994

[54] PREPARATION OF PROPENE OLIGOMERS

[75] Inventors: Hans-Joachim Mueller, Gruenstadt; Bernd L. Marczinke, Speyer; Juergen Kerth, Carlsberg; Rainer Konrad, Goennheim; Guenther Schweier, Friedelsheim; Max Strohmeyer, Limburgerhof; Bernhard Rieger, Nehren, all of Fed. Rep. of Germany

[73] Assignee: BASF Aktiengesellschaft, Ludwigshafen, Fed. Rep. of Germany

[21] Appl. No.: 22,343

[22] Filed: Feb. 25, 1993

[30] Foreign Application Priority Data

Feb. 27, 1992 [DE] Fed. Rep. of Germany ....... 4205932

[51] Int. Cl.$^5$ ............................................. C07C 2/24
[52] U.S. Cl. .................................... 585/512; 585/523
[58] Field of Search ................................ 585/512, 523

[56] References Cited

U.S. PATENT DOCUMENTS 4,542,199  9/1985  Kaminsky et al. ................... 502/117

FOREIGN PATENT DOCUMENTS 257696   3/1988  European Pat. Off. .
268214   5/1988  European Pat. Off. .
2608933  9/1977  Fed. Rep. of Germany .
3240383  5/1984  Fed. Rep. of Germany .

OTHER PUBLICATIONS

Brennstoff-Chemie, Bd. 49, Nov. 1968, Nr. 11 (323–354).
Erdol und Kohle 12, (1959) 547.
J. Am. Chem. Soc. 109, (1987) 6189.
Angew. Chem. 101, (1989) 1304.
Handbuch der Praparativen Anorganischen Chemie, vol. 2, 3rd Edition, 1395–1397 (1978).

*Primary Examiner*—Patrick P. Garvin
*Assistant Examiner*—Brent M. Peebles
*Attorney, Agent, or Firm*—Keil & Weinkauf

[57] ABSTRACT

A process for propene oligomerization catalyzed by transition metal complexes in liquid phase to give propene oligomers with a high content of terminal double bonds, comprises oligomerizing propene in the presence of a catalyst of the formula I $$Cp_2MX_2 \qquad \qquad I$$

where Cp is an unsubstituted cyclopentadienyl unit and/or a mono-$C_1$–$C_4$-alkylcyclopentadienyl unit, M is zirconium or hafnium and the ligands X are each hydride and/or halide and/or methyl, and in the presence of an aluminoxane cocatalyst, and where the ratio of the amounts of the catalyst I and the aluminoxane cocatalyst is such that the M/Al atomic ratio is from 1:250 to 1:1000, employing a temperature of from 50° to 110° C. and a pressure of from 30 to 100 bar.

4 Claims, No Drawings

PREPARATION OF PROPENE OLIGOMERS

The present invention relates to a process for propene oligomerization catalyzed by transition metal complexes in liquid phase to give propene oligomers with a high content of terminal double bonds.

It is possible with the aid of complexes of the transition metals of group IVb of the periodic table, for example the dicyclopentadienyl complexes of tetravalent titanium, zirconium or hafnium, to polymerize olefins such as ethene, propene or other 1-olefins to high molecular weight compounds in the presence of an organoaluminum cocatalyst such as methylaluminoxane (cf. DE-A 26 08 933).

Oligomeric 1-olefins, especially oligomers of propene, can be prepared catalytically in a variety of ways.

Propene can be catalytically dimerized with the aid of $\pi$-allylnickel halides in the presence of phosphines and organoaluminum compounds (Brennstoff-Chemie 49 (1968) 323). This process is very suitable for preparing propene dimers but gives only very small amounts of trimers and tetramers and therefore cannot be used to prepare them.

A process for propene oligomerization is described in Erdöl und Kohle 12, (1959) 547, in which aluminum chloride in nitromethane is used as catalyst. Most of the propene oligomers produced in this process have more than 24 carbon atoms, i.e. propene trimers or tetramers are likewise obtainable by this process only in low yield. Furthermore, the catalyst system used becomes inactive after only 7 to 8 hours and is prone to explosive spontaneous decomposition. This process is thus also unsuitable for industrial use.

J. Am. Chem. Soc. 109 (1987) 6189 discloses that propane with (R)-ethylenebis(4,5,6,7-tetrahydro-1-indenyl)dimethylzirconium and methylaluminoxane as cocatalyst in the presence of hydrogen gives saturated oligomeric alkanes.

With a similar catalyst system, namely with (S)-[1,1'-ethylenebis(4,5,6,7-tetrahydro-1-indenyl)]-zirconium bis(O-acetyl-(R)-mandelate) (56.6 mg=0.076 mmol)-/methylaluminoxane (520 mg=9 mmol of Al) dissolved in 155 ml of toluene in the absence of hydrogen it is possible, according to Angew. Chem. 101, (1989) 1304 to obtain an 88% yield of propene oligomers from 20.4 g of propene (0.48 mol). However, in order to obtain this result it is necessary to set a high catalyst/alkene ratio, i.e. the propene must be added to the catalyst very slowly, in the specific case over a period of 19 hours— since otherwise polymers are the main product.

EP-A 268 214 describes a process for preparing propene oligomers in the presence or absence of hydrogen with the aid of titanocene, zirconocene and hafnocene catalysts prepared from peralkylated cyclopentadienyl ligands, and aluminoxane cocatalysts. However, peralkylated metallocenes of this type are, just like the zirconium catalysts described above, obtainable only be elaborate syntheses, and their use in an industrial process is uneconomic because of their high cost. Titanocenes, zirconocenes and hafnocenes with unsubstituted cyclopentadienyl ligands do not, according to this publication, provide any oligomers but lead exclusively to the formation of polymers.

EP-A 257 696 discloses a process for dimerizing α-olefins such as propene with the aid of zirconocene and hafnocene catalysts in the presence of aluminoxane cocatalysts, the chosen atomic ratio of aluminum to zirconium or hafnium being from 1 to 100. A higher atomic ratio of aluminum to zirconium or hafnium leads to an increase in propene oligomers, at the expense of dimers, in the product. The productivity of the catalysts for preparing propene oligomers in this process is from 30 to 700 ml of product per g of catalyst×h, which is so low that economic preparation of propene oligomers by this process is impossible.

It is an object of the present invention to find a process for selectively preparing propene oligomers with a high content of terminal double bonds, in particular a process for selectively preparing unsaturated propene oligomers with a high content of di-, tri-, tetra- and pentamers, which can be carried out economically with the aid of a catalyst which can be prepared straightforwardly and at low cost. Moreover, the catalyst system ought to display not only high selectivity but also, in particular, high productivity.

We have found that this object is achieved by a process for propene oligomerization catalyzed by transition metal complexes in liquid phase to give propene oligomers with a high content of terminal double bonds, which comprises oligomerizing propene in the presence of a catalyst of the formula I $$Cp_2MX_2 \qquad\qquad I$$

where Cp is an unsubstituted cyclopentadienyl unit and/or a mono-$C_1$-$C_4$-alkylcyclopentadienyl unit, M is zirconium or hafnium and the ligands X are each hydride and/or halide and/or methyl, and in the presence of an aluminoxane cocatalyst, and where the ratio of the amounts of the catalyst I and the aluminoxane cocatalyst is such that the M/Al atomic ratio is from 1:250 to 1:1000, employing a temperature of from 50° to 110° C. and a pressure of from 30 to 100 bar.

The catalysts I are zirconocenes and hafnocenes, that is complexes of tetravalent zirconium and hafnium in which the metal atom M is bonded in a sandwich structure between two unsubstituted and/or $C_1$-$C_4$-monoalkyl-substituted cyclopentadienyl groups Cp, with the remaining valences of the central atom M being saturated by hydride and/or halide ions and/or by methyl groups. The zirconocene and hafnocene catalysts which are particularly preferably used in the process according to the invention are those whose cyclopentadienyl groups are unsubstituted. Halide ions which can be bonded to the metal atom are fluoride, chloride, bromide and/or iodide ions.

Examples of suitable catalysts are: $Cp_2ZrF_2$, $Cp_2ZrCl_2$, $Cp_2ZrBr_2$, $Cp_2ZrI_2$, $Cp_2ZrHCl$, $Cp_2Zr(CH_3)Cl$, $Cp_2Zr(CH_3)_2$, $Cp_2HfF_2$, $Cp_2HfCl_2$, $Cp_2HfBr_2$, $Cp_2HfI_2$, $Cp_2HfHCl$, $Cp_2Hf(CH_3)Cl$, $Cp_2Hf(CH_3)_2$.

It is expedient to employ only one catalyst in the oligomerization, but it is also possible to use mixtures of various catalysts. Preferred ligands X in the process according to the invention are chloride, hydride and methyl, and the particularly preferred central atom M for the catalysts I in the process according to the invention is zirconium. Zirconocene dichloride of the formula Ia $$Cp_2ZrCl_2 \qquad\qquad Ia$$

whose cyclopentadienyl groups are unsubstituted is particularly preferably used as catalyst I in the process according to the invention.

The catalysts I can be synthesized in a straight-forward way by known processes, e.g. as described in Brauer (editor): Handbuch der Präparativen, Anorganischen Chemie, Volume 2, 3rd edition, pages 1395 to 1397, Enke, Stuttgart 1978.

The cocatalysts used are organoaluminum compounds, preferably aluminoxanes. Aluminoxanes are formed on partial hydrolysis of organoaluminum compounds, for example those of the formula $AlR_3$, $AlR_2Y$ and $Al_2R_3Y_3$ where R can be, for example, $C_1$-$C_{10}$-alkyl, preferably $C_1$-$C_5$-alkyl, or $C_3$-$C_{10}$-cycloalkyl, $C_7$-$C_{12}$-aralkyl or -alkaryl and/or phenyl or naphthyl, and where Y can be hydrogen, halogen, preferably chlorine or bromine, or $C_1$-$C_{10}$-alkoxy, preferably methoxy or ethoxy. Partial hydrolysis of organoaluminum compounds of this type can take place by a variety of processes, e.g. that of DE-A 3 240 383 or of EP-A 268 214. The resulting oxygen-containing aluminoxanes are not in general pure compounds but mixtures of oligomers of the formula II

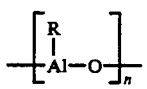

II where n is usually from 6 to 20 and R has the abovementioned meanings. Hydrolysis of organoaluminum compounds with different radicals R or mixtures of organoaluminum compounds with different radicals R results in aluminoxanes II with different radicals R, which can likewise be employed a cocatalyst in the process according to the invention. However, the aluminoxanes expediently used as cocatalysts have identical radicals R. It is also possible to use mixtures of different aluminoxanes as cocatalysts. The preferred aluminoxane in the process according to the invention is methylaluminoxane. Since the aluminoxanes used according to the invention as cocatalysts are not, owing to their mode of preparation, pure compounds, the molarity of aluminoxane solutions hereinafter is based on their aluminum content.

The amount of catalyst I relative to that of the cocatalyst employed for the oligomerization corresponds to an M/Al atomic ratio of, in general, from 1:250 to 1:1000, preferably from 1:300 to 1:600, and particularly preferably from 1:400 to 1:500.

The propene oligomerization is advantageously carried out in liquid phase and in a solvent, expediently using small amounts of a solvent, preferably an aliphatic or aromatic hydrocarbon such as benzene, toluene, xylene, ethylbenzene, cumene, naphthalene, tetralin, hexane, heptane, octane, isooctane, nonane, decane, dodecane, cyclohexane, decalin, petroleum ether or naphtha. Particularly preferred solvents are toluene and xylene. The solvent/propene ratio by volume in the process according to the invention is generally from 1:20 to 1:500, preferably from 1:30 to 1:200, and particularly preferably from 1:40 to 1:100, where the propene volume relates to its volume under the pressure applied in each case. Propene is liquid under the conditions employed.

The oligomerization according to the invention is generally carried out at from 50° to 110° C., preferably from 60° to 90° C. and under from 30 to 100 bar, preferably from 30 to 50 bar. The metallocene/propene ratio is not as a rule critical for the process according to the invention, but the metallocene/propene molar ratios are expediently from 1:50 to 1:250000, preferably from 1:70 to 1:200000, and particularly from 1:90 to 1:190000.

The process according to the invention can be carried out either batchwise, e.g. in stirred autoclaves, or continuously, for example in tubular reactors. After removal of the catalyst by distilling the product or by hydrolyzing it and subsequently filtering off the solid precipitate, the reaction mixture is expediently worked up by distillation, if required under reduced pressure.

The propene used as raw material in the process according to the invention can derive from a variety of source, e.g. from crack gases, for example from steam crackers. It is likewise possible to use the propene produced in propane dehydrogenation, for example. It is likewise possible to use propene from other sources. The propene can be employed in purified form, but it can also be employed as mixtures with other hydrocarbons which are inert under the reaction conditions.

The process according to the invention makes it possible to prepare propene oligomers with terminal double bonds selectively, in particular to prepare selectively propene oligomers with a high content of tri-, tetra- and pentamers and with high productivities.

EXAMPLES

Example 1

30 ml of 1.5 molar methylaluminoxane solution in toluene were introduced into a 2 l stirred autoclave, 900 ml (13.3 mol) of liquid propene were condensed in, and the mixture was heated to 60° C., during which the pressure rose to 20 bar. Subsequently, 40.5 mg (0.17 mmol) of zirconocene (dicyclopentadienylzirconium dichloride), dissolved in 7 ml of a 1.5 molar methylaluminoxane solution in toluene, were added and oligomerization was carried out for 60 minutes. The aluminum/zirconium atomic ratio was 250:1. The yiel was 5% ml of oligomer mixture. The productivity of the catalyst under the reaction conditions was 11900 ml of product/g of catalyst × h. Analysis of the product by gas chromatography showed the following composition:

| | |
|---|---|
| Dimers: | 17.5% |
| Trimers: | 25.9% |
| Tetramers: | 17.5% |
| Pentamers: | 6.9% |
| Hexamers: | 2.5% |
| Heptamers: | 0.5% |
| Higher oligomers: | 29.2% |

The dimers comprised 5% 2,3-dimethyl-1-butene and 91.5% 2-methyl-1-pentene. The trimers comprised 7% 2,4,-5-trimethyl-1-hexene and 87.5% 2,4-dimethyl-1-heptene. The tetramers comprised two unidentified main isomers in contents of 47.0 and 40.0% respectively. Analysis of the products by infrared and NMR spectroscopy proves that there was exclusive formation of hydrocarbons with terminal double bonds, mainly located in vinylidene groups.

Examples 2 to 4 were carried out in accordance with Example 1 by using the different aluminum/zirconium atomic ratios indicated in the table.

TABLE

| Example | Zirconocene [mmol] | Methyl-Aluminoxane [mmol] | Al/Zr atomic ratio | Productivity [ml product/ g cat × h] |
|---|---|---|---|---|
| 2 | 0.17 | 90 | 530 | 14600 |

TABLE-continued

| Example | Zirconocene [mmol] | Methyl-Aluminoxane [mmol] | Al/Zr atomic ratio | Productivity [ml product/ g cat × h] |
|---|---|---|---|---|
| 3 | 0.07 | 30 | 430 | 18600 |
| 4 | 0.07 | 60.5 | 860 | 20100 |

What is claimed is:

1. A liquid phase process for selectively producing propene dimers, trimers, tetramers and pentamers having a high content of terminal double bonds, which process comprises oligomerizing propene in the presence of a catalyst of the formula I $$Cp_2MX_2 \qquad I$$

where Cp is an unsubstituted cyclopentadienyl group and/or a mono-$C_1$-$C_4$-alkylcyclopentadienyl group, M is zirconium or hafnium and the ligands X are each hydride and/or halide and/or methyl, and in the presence of an aluminoxane cocatalyst, and where the ratio of the amounts of the catalyst I and the aluminoxane cocatalyst is such that the M/Al atomic ratio is from 1:250 to 1:1000, and wherein the process is conducted at a temperature of from 50° to 110° C. and a pressure of from 30 to 100 bar.

2. The process of claim 1, wherein zirconium is used as transition metal component of the catalyst I.

3. The process of claim 1, wherein zirconocene dichloride of the formula Ia $$Cp_2ZrCl_2 \qquad Ia$$

is employed as catalyst.

4. The process of claim 1, wherein methylaluminoxane is used as cocatalyst.

* * * * *